US00PP15498P2

(12) United States Plant Patent
Friday

(10) Patent No.: US PP15,498 P2
(45) Date of Patent: Jan. 25, 2005

(54) PEACH TREE NAMED 'P.F. 9A-007'

(50) Latin Name: *Prunus persica*
Varietal Denomination: P.F. 9A-007

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 0 days.

(21) Appl. No.: 10/702,924

(22) Filed: Nov. 7, 2003

(51) Int. Cl.[7] ..... A01H 5/00
(52) U.S. Cl. ..... Plt./198
(58) Field of Search ..... Plt./198

(56) References Cited

U.S. PATENT DOCUMENTS

PP14,778 P3 * 5/2004 Friday ..... Plt./198

OTHER PUBLICATIONS http://www.gov.on.ca/OMAFRA/english/crops/hort/news/tenderfr/tf0801a2.htm.* http://fruitgrowersnews.com/pages/2003/issue03_09/03_09_fury_peach.html.*

* cited by examiner

*Primary Examiner*—Kent Bell
*Assistant Examiner*—W C Haas

(57) ABSTRACT

A new and distinct variety of peach, *Prunus persica,* tree having the following unique combination of desirable features.

1. The new and distinct variety of peach tree is of spreading growth and a regular and productive bearer of large peaches having an average diameter of about 2¾".
2. Producing a very firm fruit having a resilient flesh texture.
3. Blossoms are partially non-showy when in full blooom.
4. A substantially spherical fruit with skin of dark red color overlying dark yellow at maturity.
5. An early season maturing fruit of good taste.
6. An early season maturing fruit of good storage and shelf life.

1 Drawing Sheet

Botanical classification: *Prunus persica.*
Varietal denomination: 'P.F. 9A-007'.

ORIGIN OF VARIETY

The new peach tree {hereinafter referred to as the 'P.F. 9A-007'} was Originated by Paul Friday in the experiment orchard, which is maintained for the purposes of breeding peach trees, in Coloma, Mich., in USDA Hardiness Zone 6a. Coloma is located in the southwest section of Michigan.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for there adaptability to local and regional growing conditions. Seeds resulting from open pollination of the trees in the experimental orchard are regularly planted in mass to produce new populations of seedlings, which are cultured and monitored to maturity. Trees with superior attributes are retained for further observation and testing, and contribute seeds to advancing generations of new populations of seedlings.

The tree of this application, 'P.F. 9A-007', was a single plant from one such a seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in the experimental orchard located in Coloma, Mich. The asexual propagation demonstrates that such reproduction of the characteristics of the tree are consistent and are established and transmitted through succeeding propagation.

SUMMARY OF THE VARIETY

The new and very distinct variety of peach tree is of moderate spreading growth and a regular and productive bearer of peaches. A distinct characteristic of the 'P.F.9A-007' peach tree is its short internodes, another notable characteristic is it's limb growth pattern producing many natural right angle crotches. The blossoms are characterized by being contracted or partially spread when in full bloom. At the same time petals of the blossoms are of lesser length than the length of petals of normal showy blossom as exemplified by the 'Loring'(non-patented) peach blossom.

The blossoms of the present peach tree at full bloom may be characterized as being partially non-showy.

Leaf glands are usually not present.

The fruit at maturity is large, having flesh of clear yellow with red around the pit and very slight red color into the flesh.

The skin is smooth having moderate down and is of dark red color overlying dark yellow. At maturity the peach is spherical having an average diameter ranging between about 2½" to 3".

The fruit has a firm flesh and may be described as resilient to the extent that the flesh is yieldable and restorable to its original state when subjected to impact forces, which may cause permanent deformities in peaches of commercial varieties. The firmness of the fruit facilitates handling and packaging of the peaches without damaging the same for shipment. This results in less spoilage and also increases the shelf life.

The fruit matures in the early part of the peach growing season in southwestern Michigan. The fruit as mentioned heretofore is of dark red color overlying dark yellow and has a very attractive appearance.

BRIEF DESCRIPTION OF THE PHOTOGRAPHS

In the accompanying drawing,

The top photograph depicts the terminal portion of the typical branch of this tree taken about the time of fruit maturity, showing the size of the leaves, the internode length, and the characteristics of the bark of the current season's growth. A tape measure is included showing the length of a leaf.

The bottom photograph shows five (5) whole fruit with one bisected across the axis showing the extent of the red coloration of flesh from the pit well. A tape measure is included to show the good size of this fruit.

DESCRIPTION OF VARIETY

The detailed botanical description of the foliage and fruit of the new variety of peach tree, as grown on its own roots, is based upon observations of the specimens grown in typical outdoor conditions at Coloma, Mich., USDA Zone 6a with the color terminology, other than the terminology expressed in common terms, in accordance with the Pantone Matching System {PMS} as used internationally to identify printed colors.

Botanical classification: *Prunus persica* cultivar 'P.F.9A-007'.

Tree:
- *Age.*—Twelve (12) years.
- *Height.*—Unpruned 13'.
- *Width.*—Unpruned 13'.
- *Size.*—Large.
- *Vigor.*—Vigorous.
- *Density.*—Medium.
- *Form.*—Upright to spreading.
- *Production.*—Good, about ⅔ of the fruit must be thinned off the tree annually; after this the tree produces about 1½ bushels of fruit per year per tree.
- *Bearer.*—Regular.
- *Disease resistance to bacterial leaf and fruit spot.*—Very resistant.

Trunk:
- *Bark.*—Dark gray (418).
- *Size.*—Medium to large.
- *Surface.*—Rough.
- *Diameter.*—7⅜" diameter — 20" above ground at 12 years of age.
- *Lenticels color.*—Pronounced.
- *Lenticels size.*—462.
- *Lenticels.*—¼" to 15⁄16".

Branches:
- *Size.*—Medium to large 3 9⁄16" to 4⅜" diameter 12" from trunk.
- *Surface.*—Rough.
- *Lenticels per square inch.*—Seven (7).
- *Lenticels color.*—407.
- *Lenticels size.*—⅛" to ⅜".
- *Crotch angles.*—Natural right angles.
- *Branch color.*—Gray (417).
- *Internode length.*—¾".

Leaves:
- *Size.*—Average length 7" average with 1⅝".
- *Form.*—Lanceolate.
- *Base.*—Acute.
- *Ape.*—Pointed.
- *Thickness.*—Medium.
- *Texture.*—Glabrous.
- *Margin.*—Serrate.
- *Petiole length.*—½".
- *Gland.*—When observed, 1 to 2 on each side of the petiole, glands seldom found.
- *Gland shape.*—When observed, slightly elongated, very shallow.
- *Gland color.*—When observed, reddish brown.
- *Leaf color.*—Upper surface green (364) — lower surface green (378).

Flower buds:
- *Size.*—7⁄16" long — ¼" wide.
- *Bud shape.*—Ovid.
- *Bud color.*—223.

Flowers:
- *Blooming period.*—Apr. 25, 2003 to Apr. 30, 2003.
- *Bloom size.*—⅞" diameter.
- *Size of petals.*—⅜" long — ¼" wide.
- *Shape of petals.*—Cupped.
- *Petal color.*—250.
- *Sepal size.*—3⁄16" long — 3⁄16" wide.
- *Sepal shape.*—Cupped.
- *Sepal color.*—417.
- *Number of anthers.*—32.
- *Anther color.*—125.
- *Number of stamens.*—32.
- *Stamen length.*—¼".
- *Stamen color.*—417.
- *Pistil length.*—5⁄16".
- *Pistil color.*—388.
- *Pollen.*—Present.
- *Number of petals.*—Five (5).
- *Flower color.*—250.
- *Number flowers per cluster.*—2.
- *Fragrance.*—Pleasant.

Fruit:
- *Maturity when described.*—Firm ripe.
- *Date of first picking.*—Jul. 22, 2003.
- *Date of last picking.*—Aug. 7, 2003.
- *Size.*—Average 2¾".
- *Form.*—Ovid.
- *Suture.*—Not pronounced.
- *Weight.*—6.9 oz.

Skin:
- *Thickness.*—Medium.
- *Texture.*—Medium.
- *Tendency to crack.*—None.
- *Down.*—Light.
- *Color.*—About 90% red (187) over dark yellow (143).

Flesh:
- *Texture.*—Firm.
- *Ripens.*—Even.
- *Flavor.*—Very good.

*Aroma.*—Pleasant, mild.
*Eating quality.*—Excellent.
*Color.*—Deep yellow (136).
*Pit cavity color.*—Red (179).

Stone:

*Type.*—Freestone.
*Size.*—1 9/16" long — 1-1/8" wide — 3/4" thick.
*Form.*—Ovid.
*Base.*—Straight.
*Apex.*—Pointed.
*Sides.*—Nearly equal.
*Surface.*—Furrowed.
*Color.*—Reddish brown (478).
*Tendency to crack.*—5%.
*Kernel.*—3/4"long — 7/16"wide — 1/16"thick.

Use: Dessert.
Shipping quality: Very good.
Keeping quality: Very good.

The tree and its fruit herein described may vary slight as a result of differences in Understood that the description of the new variety as set forth herein is that of the tree Grown under the ecological conditions prevailing at Coloma, Mich.

What is claimed is:

1. A new and distinct variety of peach tree as herein illustrated and described.

* * * * *

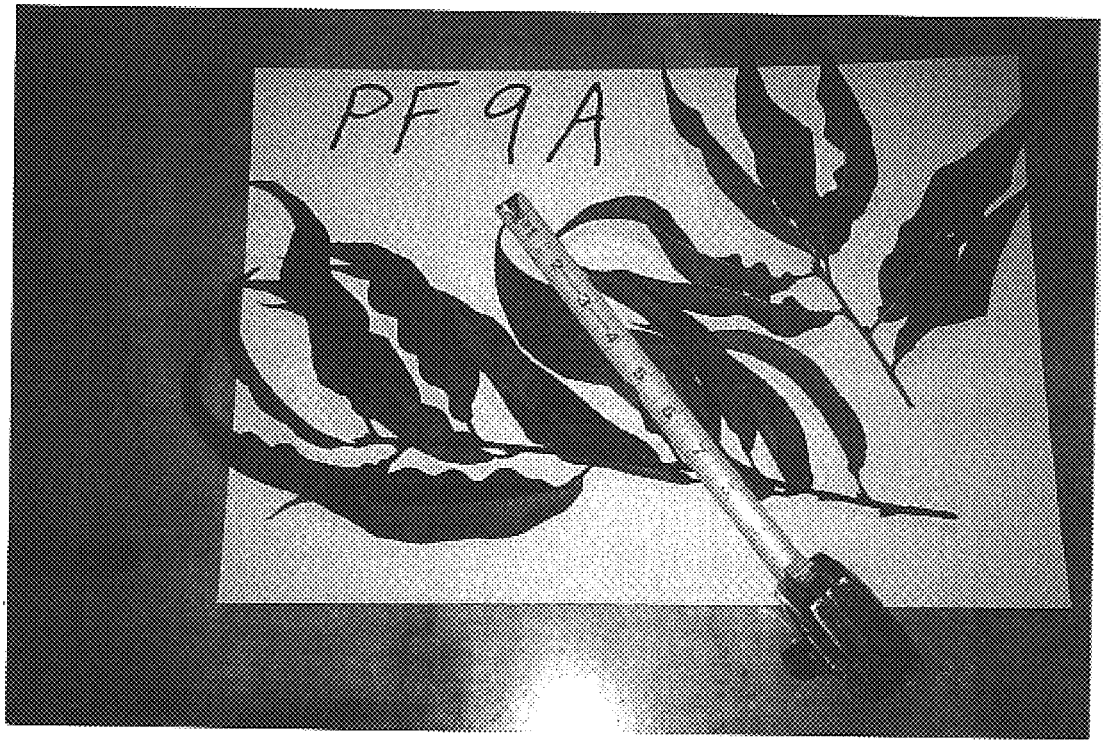
PF 9A
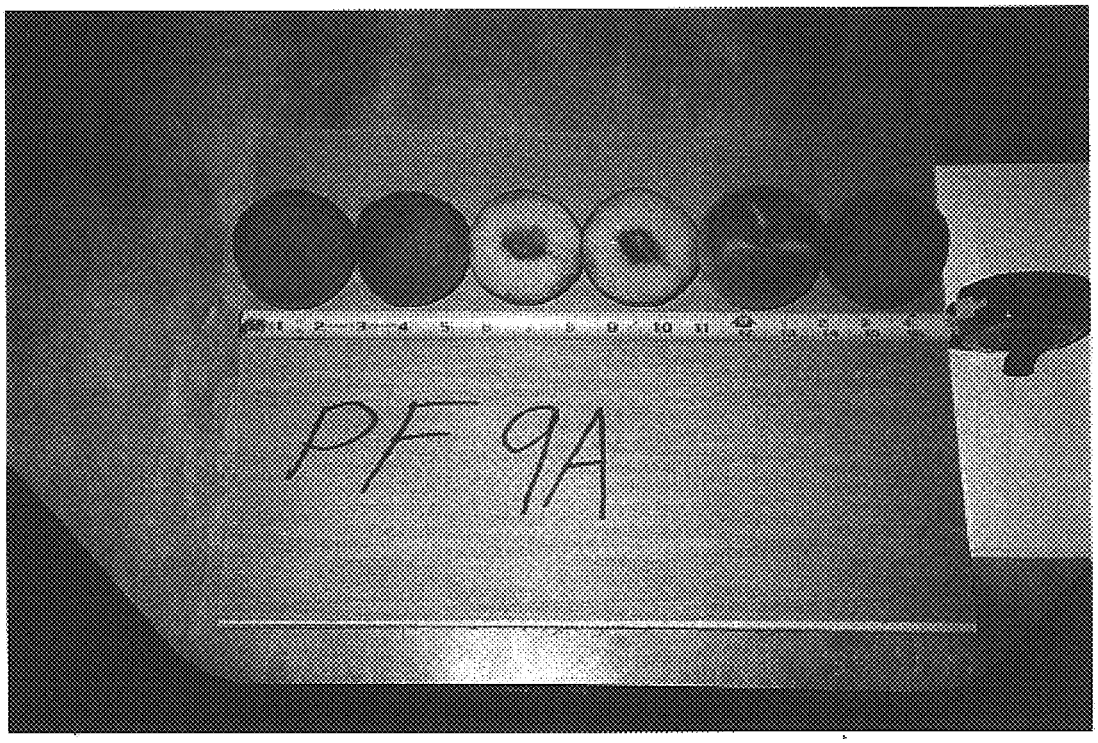
PF 9A